US00PP30172P2

(12) United States Plant Patent
Li

(10) Patent No.: US PP30,172 P2
(45) Date of Patent: Jan. 29, 2019

(54) ***LAVANDULA* PLANT NAMED 'KLELV16122'**

(50) Latin Name: *Lavandula angustifolia*
Varietal Denomination: KLELV16122

(71) Applicant: Klemm+Sohn GmbH & Co. KG, Stuttgart (DE)

(72) Inventor: Ruijun Li, North Parramatta (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/731,699

(22) Filed: Jul. 19, 2017

(51) Int. Cl.
*A01H 5/02* (2018.01)

(52) U.S. Cl.
USPC ..... Plt./445

(58) Field of Classification Search
USPC ..... Plt./445
CPC ..... A01H 6/502
See application file for complete search history.

*Primary Examiner* — Keith O. Robinson
(74) *Attorney, Agent, or Firm* — Barbara Campbell; Bethany R. Roahrig; Cochran Freund & Young LLC

(57) ABSTRACT

A new *Lavandula* plant particularly distinguished by early flowering, good branching, and long spikes, is disclosed.

1 Drawing Sheet

Genus and species: *Lavandula angustifolia.*
Variety denomination: 'KLELV16122'.

BACKGROUND OF THE NEW PLANT

The present invention comprises a new and distinct variety of *Lavandula*, botanically known as *Lavandula angustifolia*, and hereinafter referred to by the variety name 'KLELV16122'. 'KLELV16122' originated from a cross-pollination conducted in June 2010 in Cobbitty, New South Wales, Australia between the proprietary female parent 'LA10.10.01' (unpatented) and the proprietary male parent 'LA10.20.02' (unpatented).

The seeds from the cross were sown and plants were grown outdoors for evaluation, where an individual plant designated 'KLELV16122' was selected from the group of plants in May 2012 in Cobbitty, New South Wales, Australia. In May 2012 in Cobbitty, New South Wales, Australia. 'KLELV16122' was first vegetatively propagated by stem cuttings. 'KLELV16122' was found to reproduce true to type in successive generations of asexual propagation via stem cuttings.

SUMMARY

The following are the most outstanding and distinguishing characteristics of this new variety when grown under normal horticultural practices in Stuttgart, Germany.

1. Early flowering;
2. Good branching; and
3. Long spikes.

CROSS-REFERENCE TO RELATED APPLICATIONS

An application with the Community Plant Variety Rights Office was filed on Jun. 21, 2017. 'KLELV16122' has not been made publicly available or sold more than one year prior to the filing date of the instant application.

DESCRIPTION OF THE PHOTOGRAPH

This new *Lavandula* plant is illustrated by the accompanying photograph which shows the plant's overall plant habit including form, foliage, and flowers. The photograph is of a 12-week-old plant grown in a greenhouse in Stuttgart, Germany in August 2015. The colors shown are as true as can be reasonably obtained by conventional photographic procedures.

DESCRIPTION OF THE NEW VARIETY

The following detailed descriptions set forth the distinctive characteristics of 'KLELV16122'. The data which define these characteristics were collected from asexual reproductions carried out in Cobbitty, New South Wales, Australia in October 2016. Data was collected on four-month-old plants grown in a greenhouse. Color references are to The R.H.S. Colour Chart of The Royal Horticultural Society of London (R.H.S.), 5$^{th}$ edition (2007).

Classification:
- *Family.*—Asteraceae.
- *Botanical.*—*Lavandula angustifolia.*
- *Common.*—*Lavandula*, lavender.
- *Designation.*—'KLELV16122'.

Parentage:
- *Female parent.*—The proprietary female *Lavandula* variety 'LA10.10.01' (unpatented).
- *Male parent.*—The proprietary male *Lavandula* variety 'LA10.20.02' (unpatented).

Plant:
- *Propagation type.*—Vegetative cuttings.
- *Time to initiate roots.*—About 2 weeks.
- *Time to produce a rooted cutting.*—Approximately 3 to 4 weeks.
- *Root description.*—Fine, fibrous; white in color, RHS 155D.
- *Rooting habit.*—Freely branching.
- *Plant habit.*—Upright.
- *Growth rate.*—Moderate.
- *Vigor.*—Moderate.
- *Plant height.*—39.2 cm.
- *Plant diameter or spread.*—35.6 cm.

*Attitude of the outer flowering stems at full flowering of the plant.*—Erect.
*Density of the plant at full flowering.*—Medium.

Lateral branches:
*Quantity of lateral branches.*—13 to 20.
*Length.*—19.5 cm.
*Diameter.*—0.23 cm.
*Stem.*—Internode length: 1.2 cm.
*Number of internodes per branch/stem.*—About 21.
*Node length.*—0.01 cm.
*Node diameter.*—0.23 cm.
*Texture.*—Pubescent.
*Color.*—Young stems are RHS 191A; mature stems are RHS 201B.
*Stem shape.*—Square.
*Strength.*—Strong.

Leaves:
*Arrangement.*—Opposite.
*Leaf type.*—Simple.
*Quantity per main branch.*—20 pairs.
*Length.*—Average is 3.6 cm.
*Width.*—Average is 0.39 cm.
*Shape.*—Lanceolate.
*Apex.*—Acute.
*Base.*—Cuneate.
*Margin.*—Entire.
*Attachment.*—Sessile.
*Fragrance.*—Strong, lavender scent.
*Texture (both upper and lower surface).*—Pubescent.
*Immature leaf color.*—Upper surface: RHS 190B. Lower surface: RHS 190A.
*Mature leaf color.*—Upper surface: RHS 189B. Lower surface: RHS 189A.
*Venation pattern.*—Pinnate.
*Venation color (both upper and lower surfaces).*—Same as the leaf coloration.
*Petiole.*—Absent.

Flower buds:
*Length.*—About 0.5 cm.
*Diameter.*—About 0.35 cm.
*Shape.*—Oblong.
*Color.*—RHS 147C; close to RHS 94B towards the apex.
*Rate of opening.*—Average of 4 days.

Flowers:
*Form.*—Small, single flower in verticillasters arranged in spikes.
*Number of rows of flowers.*—7 to 10.
*Number of flower spikes per lateral stem.*—1.
*Average number of flowers per spike.*—Average of 90.
*Inflorescence length (excluding terminal bracts).*—Average of 9.1 cm.
*Inflorescence width (excluding terminal bracts).*—Average of 2.3 cm.
*Flower longevity.*—About 3 to 5 days.
*Self-cleaning or persistent.*—Self-cleaning.
*Fragrance.*—None detected.
*Natural flowering season.*—Late spring through summer.
*Position of flowers relative to the foliage.*—Moderately above.

Petals:
*Shape.*—Salverform.
*Quantity of petals.*—5, fused.
*Length.*—0.2 cm.
*Width.*—0.2 cm.
*Shape.*—Round.
*Apex.*—Obtuse.
*Base.*—Fused.
*Margin.*—Entire.
*Texture (both upper and lower surfaces).*—Glabrous.
*Color, immature (both upper and lower surfaces).*—RHS 94B.
*Color, mature (both upper and lower surfaces).*—RHS 94C.

Calyx:
*Quantity of sepals and arrangement.*—5, and all of the sepals are fused into a campanulate tube.
*Calyx shape.*—Lanceolate.
*Calyx length.*—0.5 cm.
*Calyx width.*—0.21 cm.
*Sepal texture.*—Upper surface: Pubescent. Lower surface: Glabrous.
*Sepal color.*—Upper surface: RHS N89B. Lower surface: RHS 146B.
*Sepal shape.*—Linear.
*Sepal apex.*—Broadly acute.
*Sepal margin.*—Entire.

Terminal bracts:
*Quantity.*—2.
*Attitude and angle of attachment.*—Each whorl of flowers subtended by dry bracts; 7 to 9 whorls per spike and each whorl is approximately 0.7 cm long and 1.3 cm wide.
*Infertile bracts of the spikes.*—Absent.
*Length.*—0.6 cm.
*Width.*—0.35 cm.
*Texture (both upper and lower surfaces).*—Smooth.
*Shape.*—Rhomboidal.
*Apex.*—Cuspidate.
*Base.*—Cuneate.
*Margin.*—Entire.
*Venation pattern.*—Parallel.
*Venation color.*—RHS 152C.
*Duration on plant.*—Has not been observed.
*Self-cleaning or persistent.*—Self-cleaning.
*Color.*—Upper surface: RHS 152C (mature). Lower surface: RHS 152C (mature).

Peduncles:
*Length.*—Average of 19.2 cm.
*Diameter.*—Average 0.24 cm.
*Strength.*—Moderate.
*Texture.*—Tomentose.
*Color.*—191A RHS.
*Aspect.*—Upright.

Reproductive organs:
*Stamens.*—Quantity per flower: 4. Filament length: 0.15 cm. Filament color: RHS 155C. Anther length: 0.03 cm. Anther diameter: 0.02 cm. Anther color: RHS N186B. Pollen amount: Moderate. Pollen color: RHS 167A.
*Pistils.*—Quantity per flower: 1. Pistil length: 0.6 cm. Style length: 0.45 cm. Style color: RHS 155A. Stigma shape: Club-shaped. Stigma length: 0.15 cm. Stigma color: RHS 92B. Ovary size: 0.15 cm. Ovary color: RHS 138A.

Fruit and seed set: None observed.

Disease and pest/insect resistance: No disease and pest/insect resistance observed.

COMPARISON WITH PARENTAL LINES AND KNOWN VARIETY

'KLELV16122' is distinguished from its parents as described in Table 1.

TABLE 1

Comparison with Parental Lines

| Characteristic | 'KLELV16122' | Female Parent 'LA10.10.01' | Male Parent 'LA10.20.02' |
|---|---|---|---|
| Earliness to flower | Early | Moderate | Early |
| Branching | Well | Average | Well |
| Spikes | Long | Long | Short |

'KLELV16122' is most similar to the commercial *Lavandula* variety 'Hidicote Blue' (unpatented). Differences between the varieties are described in Table 2.

TABLE 2

Comparison with Similar Variety

| Characteristic | 'KLELV16122' | 'Hidicote Blue' |
|---|---|---|
| Earliness to flower | Flowers 2 to 3 weeks earlier than 'Hidicote Blue' | Flowers 2 to 3 weeks later than 'KLELV16122' |
| Branching | More than 10 stems per plant | Average of 8 to 10 stems per plant |
| Spikes | More than two times longer than 'Hidicote Blue' | Shorter than 'KLELV16122' |

I claim:

1. A new and distinct variety of *Lavandula* plant designated 'KLELV16122' as illustrated and described herein.

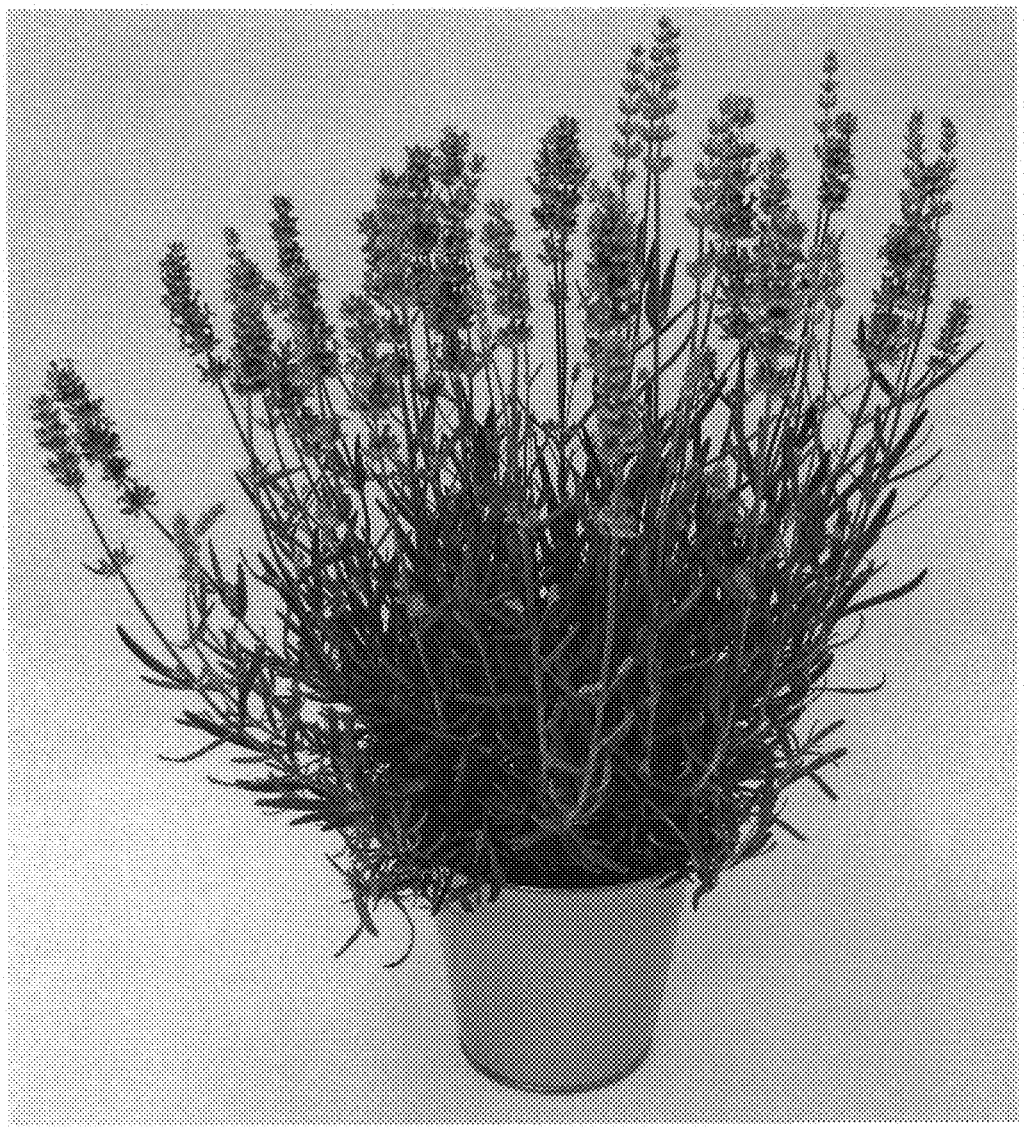

* * * * *